US009730888B2

(12) United States Patent
Pan et al.

(10) Patent No.: US 9,730,888 B2
(45) Date of Patent: Aug. 15, 2017

(54) METHOD OF ENHANCING DELIVERY OF THERAPEUTIC COMPOUNDS TO THE EYE

(71) Applicant: Wayne State University, Detroit, MI (US)

(72) Inventors: Zhuo-Hua Pan, Troy, MI (US); Elena Ivanova, White Plains, NY (US)

(73) Assignee: Wayne State University, Detroit, MI (US)

(*) Notice: Subject to any disclaimer, the term of this patent is extended or adjusted under 35 U.S.C. 154(b) by 0 days.

(21) Appl. No.: 14/777,420

(22) PCT Filed: Mar. 13, 2014

(86) PCT No.: PCT/US2014/026224
§ 371 (c)(1),
(2) Date: Sep. 15, 2015

(87) PCT Pub. No.: WO2014/160281
PCT Pub. Date: Oct. 2, 2014

(65) Prior Publication Data
US 2016/0038409 A1    Feb. 11, 2016

Related U.S. Application Data

(60) Provisional application No. 61/785,015, filed on Mar. 14, 2013.

(51) Int. Cl.
| | | |
|---|---|---|
| *A61K 48/00* | (2006.01) | |
| *A61K 9/00* | (2006.01) | |
| *A61K 38/36* | (2006.01) | |
| *A61K 31/7088* | (2006.01) | |
| *A61K 31/713* | (2006.01) | |
| *A61K 36/05* | (2006.01) | |
| *A61K 38/16* | (2006.01) | |
| *A61K 38/48* | (2006.01) | |

(52) U.S. Cl.
CPC ........ *A61K 9/0048* (2013.01); *A61K 31/7088* (2013.01); *A61K 31/713* (2013.01); *A61K 36/05* (2013.01); *A61K 38/16* (2013.01); *A61K 38/36* (2013.01); *A61K 38/484* (2013.01); *A61K 48/0008* (2013.01); *A61K 48/0075* (2013.01); *C12Y 304/21007* (2013.01)

(58) Field of Classification Search
None
See application file for complete search history.

(56) References Cited

U.S. PATENT DOCUMENTS

| | | | |
|---|---|---|---|
| 8,470,790 B2 | 6/2013 | Pan et al. | |
| 2007/0196350 A1* | 8/2007 | Bartels | A61K 9/0048 424/94.4 |

FOREIGN PATENT DOCUMENTS

| | | |
|---|---|---|
| WO | WO 00/15822 A1 | 3/2000 |
| WO | WO 2004/052228 A2 | 6/2004 |
| WO | WO 2007/005856 A1 | 1/2007 |
| WO | WO 2007/131180 A2 | 11/2007 |
| WO | WO 2009/067407 A2 | 5/2009 |
| WO | WO 2011/023805 A1 | 3/2011 |
| WO | WO 2013/134295 A1 | 9/2013 |

OTHER PUBLICATIONS

Mao et al. Hum Gene Ther 2012;23:356-66.*
Goldenberg et al. Retina 2011;31:393-400.*
Liu et al. IOVS 2011;52:4789-94.*
Altschul, S. F. et al., "Basic Local Alignment Search Tool," *Journal of Molecular Biology* (1990) 215:403-410.
Altschul, S. F. et al., "Gapped Blast and PSI-Blast: a new generation of protein database search programs," *Nucl. Acids. Res.* (1997) 25(17):3389-3402.
Balkema, G. W. et al., "Visually Evoked Eye Movements in Mouse Mutants and Inbred Strains," *Investigative Ophthalmology & Visual Science* (1984) 25(7):795-800.
Bi, A. et al., "Ectopic Expression of a Microbial-Type Rhodopsin Restores Visual Responses in Mice with Photoreceptor Degeneration," *Neuron* (2006) 50:23-33.
Boyden, E. S. et al., "Millisecond-timescale, genetically targeted optical control of neural activity," *Nature Neuroscience* (2005) 8(9):1263-1268.
GenBank Accession No. AB058890.1, Aug. 9, 2006.
GenBank Accession No. AB058891.1, Aug. 9, 2006.
GenBank Accession No. EF474018, Apr. 4, 2007.
GenBank Accession No. NM000301.3, Feb. 24, 2013.
GenBank Accession No. NP000292.1, Feb. 24, 2013.
Ivanova, E. et al., "Evaluation of AAV-Mediated Expression of Chop2-GFP in the Marmoset Retina," *IOVS* (2010) 51(10):5288-5296.
McLaughlin, S. K. et al., "Adeno-Associated Virus General Transduction Vectors: Analysis of Proviral Structures," *Journal of Virology* (1998) 62(6):1963-1973.
Mitchiner, J. C. et al., "Visually Evoked Eye Movements in the Mouse (*Mus musculus*)," *Vision Res.* (1976) 16:1169-1171.
Nagel, G. et al., "Channelrhodopsin-1: A Light-Gated Proton Channel in Green Algae," *Science* (2002) 296:2395-2398.
Nagel, G. et al., "Channelrhodopsin-2, a directly light-gated cation-selective membrane channel," *PNAS* (2003) 100(24):13940-13945.
Petrs-Silva, H. et al., "Novel Properties of Tyrosine-mutant AAV2 Vectors in the Mouse Retina," *Molecular Therapy* (2011) 19(2):293-301.
U.S. Appl. No. 61/951,360, filed Mar. 11, 2014, 38 pages.
GenBank Accession No. AF147789, Mar. 10, 2010.

(Continued)

*Primary Examiner* — Janice Li
(74) *Attorney, Agent, or Firm* — Cooley LLP; Ivor Elrifi; Cynthia Kozakiewicz

(57) ABSTRACT

The invention provides methods for enhancing the delivery of therapeutic compounds to the eye of a subject by administering plasmin or derivatives thereof and the therapeutic compounds to the eye.

20 Claims, 5 Drawing Sheets

(56) References Cited

OTHER PUBLICATIONS

Hayes, Jm et al., "Elevated Dark-Adapted Thresholds in Hypopigmented Mice Measured with a Water Maze Screening Apparatus" Behavor Genetics vol. 23, pp. 395-403 No. 4, (1993).

\* cited by examiner

SEQUENCE LISTING

```
<160> NUMBER OF SEQ ID NOS: 9

<210> SEQ ID NO 1
<211> LENGTH: 809
<212> TYPE: PRT
<213> ORGANISM: Homo sapiens

<400> SEQUENCE: 1

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240
```

-continued

```
Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Gly Asn Val Ala Val
        275                 280                 285

Thr Val Ser Gly His Thr Cys Gln His Trp Ser Ala Gln Thr Pro His
    290                 295                 300

Thr His Asn Arg Thr Pro Glu Asn Phe Pro Cys Lys Asn Leu Asp Glu
305                 310                 315                 320

Asn Tyr Cys Arg Asn Pro Asp Gly Lys Arg Ala Pro Trp Cys His Thr
                325                 330                 335

Thr Asn Ser Gln Val Arg Trp Glu Tyr Cys Lys Ile Pro Ser Cys Asp
            340                 345                 350

Ser Ser Pro Val Ser Thr Glu Gln Leu Ala Pro Thr Ala Pro Pro Glu
        355                 360                 365

Leu Thr Pro Val Val Gln Asp Cys Tyr His Gly Asp Gly Gln Ser Tyr
    370                 375                 380

Arg Gly Thr Ser Ser Thr Thr Thr Thr Gly Lys Lys Cys Gln Ser Trp
385                 390                 395                 400

Ser Ser Met Thr Pro His Arg His Gln Lys Thr Pro Glu Asn Tyr Pro
                405                 410                 415

Asn Ala Gly Leu Thr Met Asn Tyr Cys Arg Asn Pro Asp Ala Asp Lys
            420                 425                 430

Gly Pro Trp Cys Phe Thr Thr Asp Pro Ser Val Arg Trp Glu Tyr Cys
        435                 440                 445

Asn Leu Lys Lys Cys Ser Gly Thr Glu Ala Ser Val Val Ala Pro Pro
    450                 455                 460

Pro Val Val Leu Leu Pro Asp Val Glu Thr Pro Ser Glu Glu Asp Cys
465                 470                 475                 480

Met Phe Gly Asn Gly Lys Gly Tyr Arg Gly Lys Arg Ala Thr Thr Val
                485                 490                 495

Thr Gly Thr Pro Cys Gln Asp Trp Ala Ala Gln Glu Pro His Arg His
            500                 505                 510

Ser Ile Phe Thr Pro Glu Thr Asn Pro Arg Ala Gly Leu Glu Lys Asn
        515                 520                 525

Tyr Cys Arg Asn Pro Asp Gly Asp Val Gly Gly Pro Trp Cys Tyr Thr
    530                 535                 540

Thr Asn Pro Arg Lys Leu Tyr Asp Tyr Cys Asp Val Pro Gln Cys Ala
545                 550                 555                 560

Ala Pro Ser Phe Asp Cys Gly Lys Pro Gln Val Glu Pro Lys Lys Cys
                565                 570                 575

Pro Gly Arg Val Val Gly Gly Cys Val Ala His Pro His Ser Trp Pro
            580                 585                 590

Trp Gln Val Ser Leu Arg Thr Arg Phe Gly Met His Phe Cys Gly Gly
        595                 600                 605

Thr Leu Ile Ser Pro Glu Trp Val Leu Thr Ala Ala His Cys Leu Glu
    610                 615                 620

Lys Ser Pro Arg Pro Ser Ser Tyr Lys Val Ile Leu Gly Ala His Gln
625                 630                 635                 640

Glu Val Asn Leu Glu Pro His Val Gln Glu Ile Glu Val Ser Arg Leu
                645                 650                 655
```

```
Phe Leu Glu Pro Thr Arg Lys Asp Ile Ala Leu Leu Lys Leu Ser Ser
                660                 665                 670
Pro Ala Val Ile Thr Asp Lys Val Ile Pro Ala Cys Leu Pro Ser Pro
            675                 680                 685
Asn Tyr Val Val Ala Asp Arg Thr Glu Cys Phe Ile Thr Gly Trp Gly
        690                 695                 700
Glu Thr Gln Gly Thr Phe Gly Ala Gly Leu Leu Lys Glu Ala Gln Leu
705                 710                 715                 720
Pro Val Ile Glu Asn Lys Val Cys Asn Arg Tyr Glu Phe Leu Asn Gly
                725                 730                 735
Arg Val Gln Ser Thr Glu Leu Cys Ala Gly His Leu Ala Gly Gly Thr
            740                 745                 750
Asp Ser Cys Gln Gly Asp Ser Gly Gly Pro Leu Val Cys Phe Glu Lys
        755                 760                 765
Asp Lys Tyr Ile Leu Gln Gly Val Thr Ser Trp Gly Leu Gly Cys Ala
        770                 775                 780
Arg Pro Asn Lys Pro Gly Val Tyr Val Arg Val Ser Arg Phe Val Thr
785                 790                 795                 800
Trp Ile Glu Gly Val Met Arg Asn Asn
                805
```

<210> SEQ ID NO 2
<211> LENGTH: 3538
<212> TYPE: DNA
<213> ORGANISM: Homo sapiens

<400> SEQUENCE: 2

```
gaatcattaa cttaatttga ctatctggtt tgtggatgcg tttactctca tgtaagtcaa      60
caacatcctg ggattgggac ccactttctg ggcactgctg ccagtccca aaatggaaca     120
taaggaagtg gttcttctac ttcttttatt tctgaaatca ggtcaaggag agcctctgga     180
tgactatgtg aatacccagg gggcttcact gttcagtgtc actaagaagc agctgggagc     240
aggaagtata gaagaatgtg cagcaaaatg tgaggaggac gaagaattca cctgcagggc     300
attccaatat cacagtaaag agcaacaatg tgtgataatg gctgaaaaca ggaagtcctc     360
cataatcatt aggatgagag atgtagtttt atttgaaaag aaagtgtatc tctcagagtg     420
caagactggg aatggaagaa actacagagg gacgatgtcc aaaacaaaaa atggcatcac     480
ctgtcaaaaa tggagttcca cttctccca cagacctaga ttctcacctg ctacacaccc     540
ctcagaggga ctggaggaga actactgcag gaatccagac aacgatccgc aggggccctg     600
gtgctatact actgatccag aaaagagata tgactactgc gacattcttg agtgtgaaga     660
ggaatgtatg cattgcagtg gagaaaaacta tgacggcaaa atttccaaga ccatgtctgg     720
actgaatgc caggcctggg actctcagag cccacacgct catggataca ttccttccaa     780
atttccaaac aagaacctga agaagaatta ctgtcgtaac cccgataggg agctgcggcc     840
ttggtgtttc accaccgacc ccaacaagcg ctgggaactt gtgacatcc ccgctgcac     900
aacacctcca ccatcttctg gtcccaccta ccagtgtctg aagggaacag gtgaaaacta     960
tcgcgggaat gtggctgtta ccgtgtccgg gcacacctgt cagcactgga gtgcacagac    1020
ccctcacaca cataacagga caccagaaaa cttcccctgc aaaaattgg atgaaaacta    1080
ctgccgcaat cctgacggaa aaggggcccc atggtgccat acaaccaaca gccaagtgcg    1140
gtgggagtac tgtaagatac cgtcctgtga ctcctcccca gtatccacgg aacaattggc    1200
tcccacagca ccacctgagc taaccccgtg ggtccaggac tgctaccatg gtgatggaca    1260
```

```
gagctaccga ggcacatcct ccaccaccac cacaggaaag aagtgtcagt cttggtcatc    1320
tatgacacca caccggcacc agaagacccc agaaaactac ccaaatgctg gcctgacaat    1380
gaactactgc aggaatccag atgccgataa aggcccctgg tgttttacca cagaccccag    1440
cgtcaggtgg gagtactgca acctgaaaaa atgctcagga acagaagcga gtgttgtagc    1500
acctccgcct gttgtcctgc ttccagatgt agagactcct tccgaagaag actgtatgtt    1560
tgggaatggg aaaggatacc gaggcaagag ggcgaccact gttactggga cgccatgcca    1620
ggactgggct gcccaggagc cccatagaca cagcattttc actccagaga caaatccacg    1680
ggcgggtctg gaaaaaaatt actgccgtaa ccctgatggt gatgtaggtg gtccctggtg    1740
ctacacgaca aatccaagaa aactttacga ctactgtgat gtccctcagt gtgcggcccc    1800
ttcatttgat tgtgggaagc tcaagtggag gccgaagaaa tgtcctggaa gggttgtagg    1860
ggggtgtgtg gcccacccac attcctggcc ctggcaagtc agtcttagaa caaggtttgg    1920
aatgcacttc tgtggaggca ccttgatatc cccagagtgg gtgttgactg ctcccactg    1980
cttggagaag tccccaaggc cttcatccta caaggtcatc ctgggtgcac accaagaagt    2040
gaatctcgaa ccgcatgttc aggaaataga agtgtctagg ctgttcttgg agcccacacg    2100
aaaagatatt gccttgctaa agctaagcag tcctgccgtc atcactgaca aagtaatccc    2160
agcttgtctg ccatcccaa attatgtggt cgctgaccgg accgaatgtt tcatcactgg    2220
ctggggagaa acccaaggta cttttggagc tggccttctc aaggaagccc agctccctgt    2280
gattgagaat aaagtgtgca atcgctatga gtttctgaat ggaagagtcc aatccaccga    2340
actctgtgct gggcatttgg ccggaggcac tgacagttgc cagggtgaca gtggaggtcc    2400
tctggttttgc ttcgagaagg acaaatacat tttacaagga gtcacttctt ggggtcttgg    2460
ctgtgcacgc cccaataagc ctggtgtcta tgttcgtgtt tcaaggtttg ttacttggat    2520
tgagggagtg atgagaaata attaattgga cgggagacag agtgacgcac tgactcacct    2580
agaggctgga acgtgggtag ggatttagca tgctggaaat aactggcagt aatcaaacga    2640
agacactgtc cccagctacc agctacgcca aacctcggca tttttttgtgt tattttctga    2700
ctgctggatt ctgtagtaag gtgacatagc tatgacattt gttaaaaata aactctgtac    2760
ttaactttga tttgagtaaa ttttggtttt ggtcttcaac attttcatgc tctttgttca    2820
ccccaccaat ttttaaatgg gcagatgggg ggatttagct gcttttgata aggaacagct    2880
gcacaaagga ctgagcaggc tgcaaggtca cagaggggag agccaagaag ttgtccacgc    2940
atttacctca tcagctaacg agggcttgac atgcattttt actgtcttta ttcctgacac    3000
tgagatgaat gttttcaaag ctgcaacatg tatgggagt catgcaaacc gattctgtta    3060
ttgggaatga aatctgtcac cgactgcttg acttgagccc aggggacacg gagcagagag    3120
ctgtatatga tggagtgaac cggtccatgg atgtgtaaca caagaccaac tgagagtctg    3180
aatgttattc tggggcacac gtgagtctag gattggtgcc aagagcatgt aaatgaacaa    3240
caagcaaata ttgaaggtgg accacttatt tcccattgct aattgcctgc ccggttttga    3300
aacagtctgc agtacacacg gtcacaggag aatgacctgt gggagagata catgtttaga    3360
aggaagagaa aggacaaagg cacacgtttt accatttaaa atattgttac caaacaaaaa    3420
tatccattca aaatacaatt taacaatgca acagtcatct tacagcagag aaatgcagag    3480
aaaagcaaaa ctgcaagtga ctgtgaataa agggtgaatg tagtctcaaa tcctcaaa    3538
```

<210> SEQ ID NO 3

```
<211> LENGTH: 19
<212> TYPE: PRT
<213> ORGANISM: Homo sapiens

<400> SEQUENCE: 3

Met Glu His Lys Glu Val Val Leu Leu Leu Leu Phe Leu Lys Ser
1               5                   10                  15

Gly Gln Gly

<210> SEQ ID NO 4
<211> LENGTH: 561
<212> TYPE: PRT
<213> ORGANISM: Homo sapiens

<400> SEQUENCE: 4

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
                100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
    195                 200                 205

Asn Leu Lys Lys Asn Tyr Cys Arg Asn Pro Asp Arg Glu Leu Arg Pro
210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
    275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320
```

```
Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
        340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg

<210> SEQ ID NO 5
<211> LENGTH: 483
<212> TYPE: PRT
<213> ORGANISM: Homo sapiens

<400> SEQUENCE: 5

Val Tyr Leu Ser Glu Cys Lys Thr Gly Asn Gly Lys Asn Tyr Arg Gly
1               5                  10                  15

Thr Met Ser Lys Thr Lys Asn Gly Ile Thr Cys Gln Lys Trp Ser Ser
            20                  25                  30

Thr Ser Pro His Arg Pro Arg Phe Ser Pro Ala Thr His Pro Ser Glu
        35                  40                  45

Gly Leu Glu Glu Asn Tyr Cys Arg Asn Pro Asp Asn Asp Pro Gln Gly
    50                  55                  60

Pro Trp Cys Tyr Thr Thr Asp Pro Glu Lys Arg Tyr Asp Tyr Cys Asp
65                  70                  75                  80

Ile Leu Glu Cys Glu Glu Glu Cys Met His Cys Ser Gly Glu Asn Tyr
                85                  90                  95

Asp Gly Lys Ile Ser Lys Thr Met Ser Gly Leu Glu Cys Gln Ala Trp
                100                 105                 110

Asp Ser Gln Ser Pro His Ala His Gly Tyr Ile Pro Ser Lys Phe Pro
            115                 120                 125
```

```
Asn Lys Asn Leu Lys Lys Asn Tyr Cys Arg Asn Pro Asp Arg Glu Leu
    130                 135                 140

Arg Pro Trp Cys Phe Thr Thr Asp Pro Asn Lys Arg Trp Glu Leu Cys
145                 150                 155                 160

Asp Ile Pro Arg Cys Thr Thr Pro Pro Ser Ser Gly Pro Thr Tyr
                165                 170                 175

Gln Cys Leu Lys Gly Thr Gly Glu Asn Tyr Arg Gly Asn Val Ala Val
            180                 185                 190

Thr Val Ser Gly His Thr Cys Gln His Trp Ser Ala Gln Thr Pro His
        195                 200                 205

Thr His Asn Arg Thr Pro Glu Asn Phe Pro Cys Lys Asn Leu Asp Glu
    210                 215                 220

Asn Tyr Cys Arg Asn Pro Asp Gly Lys Arg Ala Pro Trp Cys His Thr
225                 230                 235                 240

Thr Asn Ser Gln Val Arg Trp Glu Tyr Cys Lys Ile Pro Ser Cys Asp
                245                 250                 255

Ser Ser Pro Val Ser Thr Glu Gln Leu Ala Pro Thr Ala Pro Pro Glu
            260                 265                 270

Leu Thr Pro Val Val Gln Asp Cys Tyr His Gly Asp Gly Gln Ser Tyr
        275                 280                 285

Arg Gly Thr Ser Ser Thr Thr Thr Gly Lys Lys Cys Gln Ser Trp
    290                 295                 300

Ser Ser Met Thr Pro His Arg His Gln Lys Thr Pro Glu Asn Tyr Pro
305                 310                 315                 320

Asn Ala Gly Leu Thr Met Asn Tyr Cys Arg Asn Pro Asp Ala Asp Lys
                325                 330                 335

Gly Pro Trp Cys Phe Thr Thr Asp Pro Ser Val Arg Trp Glu Tyr Cys
            340                 345                 350

Asn Leu Lys Lys Cys Ser Gly Thr Glu Ala Ser Val Val Ala Pro Pro
        355                 360                 365

Pro Val Val Leu Leu Pro Asp Val Glu Thr Pro Ser Glu Glu Asp Cys
    370                 375                 380

Met Phe Gly Asn Gly Lys Gly Tyr Arg Gly Lys Arg Ala Thr Thr Val
385                 390                 395                 400

Thr Gly Thr Pro Cys Gln Asp Trp Ala Ala Gln Glu Pro His Arg His
                405                 410                 415

Ser Ile Phe Thr Pro Glu Thr Asn Pro Arg Ala Gly Leu Glu Lys Asn
            420                 425                 430

Tyr Cys Arg Asn Pro Asp Gly Asp Val Gly Gly Pro Trp Cys Tyr Thr
        435                 440                 445

Thr Asn Pro Arg Lys Leu Tyr Asp Tyr Cys Asp Val Pro Gln Cys Ala
    450                 455                 460

Ala Pro Ser Phe Asp Cys Gly Lys Pro Gln Val Glu Pro Lys Lys Cys
465                 470                 475                 480

Pro Gly Arg

<210> SEQ ID NO 6
<211> LENGTH: 78
<212> TYPE: PRT
<213> ORGANISM: Homo sapiens

<400> SEQUENCE: 6

Glu Pro Leu Asp Asp Tyr Val Asn Thr Gln Gly Ala Ser Leu Phe Ser
1               5                   10                  15
```

```
Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys
65                  70                  75
```

<210> SEQ ID NO 7
<211> LENGTH: 230
<212> TYPE: PRT
<213> ORGANISM: Homo sapiens

<400> SEQUENCE: 7

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg Asn Asn
225                 230
```

<210> SEQ ID NO 8
<211> LENGTH: 19
<212> TYPE: PRT
<213> ORGANISM: Artificial Sequence
<220> FEATURE:
<223> OTHER INFORMATION: Recombinant truncated form of human plasmin

<400> SEQUENCE: 8

```
Ala Pro Ser Phe Asp Cys Gly Lys Pro Gln Val Glu Pro Lys Lys Cys
1               5                   10                  15

Pro Gly Arg
```

```
<210> SEQ ID NO 9
<211> LENGTH: 230
<212> TYPE: PRT
<213> ORGANISM: Artificial Sequence
<220> FEATURE:
<223> OTHER INFORMATION: Recombinant truncated form of human plasmin

<400> SEQUENCE: 9

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
                100                 105                 110

Val Ala Asp Arg Thr Glu Cys Phe Ile Thr Gly Trp Gly Glu Thr Gln
            115                 120                 125

Gly Thr Phe Gly Ala Gly Leu Leu Lys Glu Ala Gln Leu Pro Val Ile
        130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg Asn Asn
225                 230
```

METHOD OF ENHANCING DELIVERY OF THERAPEUTIC COMPOUNDS TO THE EYE

RELATED APPLICATIONS

This application claims priority to, and benefit of, the U.S. Provisional Application No. 61/785,015 filed on Mar. 14, 2013; the contents of which are hereby incorporated by reference in its entirety.

GOVERNMENT SUPPORT

This invention was made with government support under EY017130 awarded by the National Institutes of Health. The government has certain rights in the invention.

FIELD OF THE INVENTION

This invention relates generally to methods of enhancing the delivery of therapeutic compounds to the eye.

BACKGROUND OF THE INVENTION

The eye is a complex optical system that detects light, converts the light to a set of electrical signals, and transmits these signals to the brain, ultimately generating a representation of our world. Ocular diseases and disorders can cause diminished visual acuity, diminished light sensitivity, and blindness.

Delivery of therapeutic compounds to specific ocular tissues affected by an ocular disease or disorder, such as the retina, is a challenge. Current methods, such as intravitreal injection or implanted drug delivery devices, are still limited in the efficacy of delivery. Specifically, the therapeutic agents are often localized only to the immediate areas surrounding the delivery site, and fail to permeate or diffuse beyond intervening ocular structures or throughout the targeted ocular tissue, thereby severely limiting the efficacy of such therapeutics. Thus, there exists a long-felt need for methods to enhance the delivery of therapeutic compounds to the eye.

SUMMARY OF THE INVENTION

The invention provides a solution for the long-felt need for methods to enhance or improve the delivery of therapeutic compounds to the eye.

The present invention features a method of enhancing the delivery of a therapeutic agent to an eye of a subject by administering a plasmin or derivative thereof and the therapeutic agent to the eye. The present invention also features the use of a composition comprising a plasmin or derivative thereof for delivery to the eye of a subject for enhancing the delivery of a therapeutic agent.

In one aspect, the plasmin or derivative thereof is a miniplasmin or a microplasmin (Ocriplasmin). The plasmin or derivative thereof encompassed in the present invention includes amino acid sequences SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9 or functional variants or fragments thereof.

In one aspect, the therapeutic agent is selected from a small molecule, a nucleic acid, an antibody, or a peptide. The nucleic acid is a nucleic acid expression vector (i.e., a viral vector), a plasmid, or an siRNA. For example, the viral vector is a AAV viral vector (i.e., recombinant AAV or rAAV) that encodes a transgene. Preferably, the transgene encodes a gene product that increases or restores light sensitivity, increases light detection, increases photosensitivity, increases visual evoked potential, or restores vision to the blind. More preferably, the transgene is an opsin gene. Examples of opsin genes include, but are not limited to, channelrhodopsins (i.e., channelrhodopsin-1, channelrhodopsin-2, *Volvox carteri* channelrhodopsins 1 or 2), melanopsin, pineal opsin, photopsins, halorhodopsin, bacteriorhodopsin, proteorhodopsin, or any functional variants or fragments thereof.

Other examples of therapeutic agents include, but are not limited to ranibizumab antibody FAB (Lucentis), VEGF Trap fusion molecule (VEGF Trap-Eye), macugen pegylated polypeptide (Pegaptanib), and bevacimzumab (Avastin). Any of the therapeutic agents used in the present invention may be encapsulated in a nanoparticle, a polymer, or a liposome.

In one aspect, the plasmin or derivative thereof and the therapeutic agent are delivered concurrently or sequentially.

The present invention provides a method in which the therapeutic agent is delivered to a retinal cell. The retinal cell is a retinal ganglion cell, a retinal horizontal cell, a retinal bipolar cell, an amacrine cell, a photoreceptor cell, a Müller glial cell, or a retinal pigment epithelial cell.

In one aspect, the plasmin or derivative thereof and the therapeutic agent is administered to the vitreous of the eye.

The present invention further provides a method of increasing or restoring light sensitivity in a subject comprising administering a plasmin or derivative thereof and a viral vector that encodes an opsin to the vitreous of the eye. The present invention also provides a method of improving or restoring vision in a subject comprising administering a plasmin or derivative thereof and a viral vector that encodes an opsin to the vitreous of the eye.

Uses of a composition comprising a plasmin or derivative thereof for treating an ocular disease or disorder in a subject are also provided herein.

The subject is suffering from an ocular disease or disorder. Preferably, the ocular disease or disorder is associated with photoreceptor degeneration.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and are encompassed by the following detailed description and claims.

DETAILED DESCRIPTION

Figure 1:
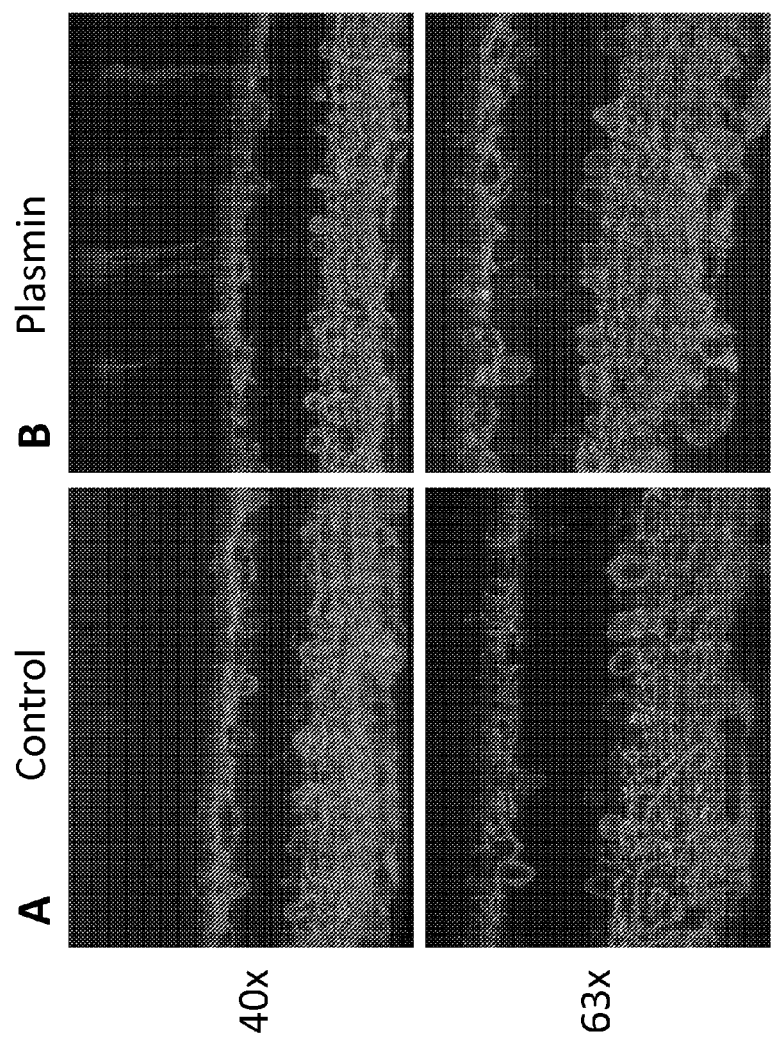
FIG. 1 is a series of representative GFP fluorescence images in retinal vertical sections after intravitreal injection of AAV2 vectors ($6 \times 10^{12}$ vg/ml), AAV2/2-ChR2-GFP-WPRE-hGHpA, in control (A, B) or co-injection with plasmin (0.0251 U/eye) (C, D). The vectors were co-injected along with plasmin into the vitreous space of adult C56BL/6J mice at age of approximately one month. Transduction efficiency was evaluated one month after virus injection by immunostaining and cell counting.

The present invention provides methods for enhanced delivery of therapeutic compounds or agents to the eye of a subject by administering a plasmin or derivative thereof and the therapeutic agent to the eye. In some embodiments, the plasmin or derivative thereof and the therapeutic agent may be delivered to the vitreous for enhanced delivery to the retina and retinal cells. The retinal cells include, for example, photoreceptor cells (e.g., rods, cones, and photosensitive retinal ganglion cells), horizontal cells, retinal bipolar cells, amacrine cells, retinal ganglion cells, Müller glial cells, and retinal pigment epithelial cells. In other embodiments, the plasmin or derivative thereof and the therapeutic agent may be delivered to, for example, the posterior segment, the anterior segment, the sclera, the choroid, the conjunctiva, the iris, the lens, or the cornea.

The retina is a complex tissue in the back of the eye that contains specialized photoreceptor cells called rods and cones. The photoreceptors connect to a network of nerve cells for the local processing of visual information. This information is sent to the brain for decoding into a visual image. The retina is susceptible to a variety of diseases, including age-related macular degeneration (AMD), diabetic retinopathy (DR), retinitis pigmentosa (RP), glaucoma, and other inherited retinal degenerations, uveitis, retinal detachment, and eye cancers (ocular melanoma and retinoblastoma). Each of these can lead to visual loss or complete blindness.

Delivery of therapeutic compounds to the retina is a challenge, due to the complex structure of the eye. Intravitreal injection and vitreal delivery devices are frequently used to deliver therapeutic compounds to the retina, however the efficiency of delivery is impaired by the inner limiting membrane (ILM) and the multiple layers of cells of the retina.

Plasmin

Plasmin is a serine protease that is present in the blood that degrades fibrin blood clots and other blood plasma proteins. Specifically, plasmin cleaves fibrin, fibronectin, thrombospondin, laminin, proaccelerin, and Von Willebrand Factor (VWF) into soluble products. Plasmin exhibits preferential cleavage at the carboxyl side of Lysine and Arginine residues with higher selectivity than trypsin.

Specifically, plasmin originates from a zymogen, or inactive precursor protein, called plasminogen (PLG). The amino acid sequence of plasminogen is known in the art, for example, Genbank Accession Number NP_000292, and listed below:

```
                                            (SEQ ID NO: 1)
MEHKEVVLLLLLFLKSGQGEPLDDYVNTQGASLFSVTKKQLGAGSIEECA

AKCEEDEEFTCRAFQYHSKEQQCVIMAENRKSSIIIRMRDVVLFEKKVYL

SECKTGNGKNYRGTMSKTKNGITCQKWSSTSPHRPRFSPATHPSEGLEEN

YCRNPDNDPQGPWCYTTDPEKRYDYCDILECEEECMHCSGENYDGKISKT

MSGLECQAWDSQSPHAHGYIPSKFPNKNLKKNYCRNPDRELRPWCFTTDP

NKRWELCDIPRCTTPPPSSGPTYQCLKGTGENYGNVAVTVSGHTCQHWSA

QTPHTHNRTPENFPCKNLDENYCRNPDGKRAPWCHTTNSQVRWEYCKIPS

CDSSPVSTEQLAPTAPPELTPVVQDCYHGDGQSYRGTSSTTTTGKKCQSW

SSMTPHRHQKTPENYPNAGLTMNYCRNPDADKGPWCFTTDPSVRWEYCNL

KKCSGTEASVVAPPPVVLLPDVETPSEEDCMFGNGKGYRGKRATTVTGTP

CQDWAAQEPHRHSIFTPETNPRAGLEKNYCRNPDGDVGGPWCYTTNPRKL

YDYCDVPQCAAPSFDCGKPQVEPKKCPGRVVGGCVAHPHSWPWQVSLRTR

FGMHFCGGTLISPEWVLTAAHCLEKSPRPSSYKVILGAHQEVNLEPHVQE

IEVSRLFLEPTRKDIALLKLSSPAVITDKVIPACLPSPNYVVADRTECFI

TGWGETQGTFGAGLLKEAQLPVIENKVCNRYEFLNGRVQSTELCAGHLAG

GTDSCQGDSGGPLVCFEKDKYILQGVTSWGLGCARPNKPGVYVRVSRFVT

WIEGVMRNN
```

The nucleic acid of plasminogen is known in the art, for example, Genbank Accession Number NM_000301, and as listed below:

```
                                            (SEQ ID NO: 2)
GAATCATTAACTTAATTTGACTATCTGGTTTGTGGATGCGTTTACTCTCA

TGTAAGTCAACAACATCCTGGGATTGGGACCCACTTTCTGGGCACTGCTG

GCCAGTCCCAAAATGGAACATAAGGAAGTGGTTCTTCTACTTCTTTTATT

TCTGAAATCAGGTCAAGGAGAGCCTCTGGATGACTATGTGAATACCCAGG

GGGCTTCACTGTTCAGTGTCACTAAGAAGCAGCTGGGAGCAGGAAGTATA
```

-continued

```
GAAGAATGTGCAGCAAAATGTGAGGAGGACGAAGAATTCACCTGCAGGGC

ATTCCAATATCACAGTAAAGAGCAACAATGTGTGATAATGGCTGAAAACA

GGAAGTCCTCCATAATCATTAGGATGAGAGATGTAGTTTTATTTGAAAAG

AAAGTGTATCTCTCAGAGTGCAAGACTGGGAATGGAAAGAACTACAGAGG

GACGATGTCCAAAACAAAAAATGGCATCACCTGTCAAAAATGGAGTTCCA

CTTCTCCCCACAGACCTAGATTCTCACCTGCTACACACCCCTCAGAGGGA

CTGGAGGAGAACTACTGCAGGAATCCAGACAACGATCCGCAGGGGCCCTG

GTGCTATACTACTGATCCAGAAAAGAGATATGACTACTGCGACATTCTTG

AGTGTGAAGAGGAATGTATGCATTGCAGTGGAGAAAACTATGACGGCAAA

ATTTCCAAGACCATGTCTGGACTGGAATGCCAGGCCTGGGACTCTCAGAG

CCCACACGCTCATGGATACATTCCTTCCAAATTTCCAAACAAGAACCTGA

AGAAGAATTACTGTCGTAACCCCGATAGGGAGCTGCGGCCTTGGTGTTTC

ACCACCGACCCCAACAAGCGCTGGGAACTTTGTGACATCCCCGCTGCAC

AACACCTCCACCATCTTCTGGTCCCACCTACCAGTGTCTGAAGGGAACAG

GTGAAAACTATCGCGGGAATGTGGCTGTTACCGTGTCCGGGCACACCTGT

CAGCACTGGAGTGCACAGACCCCTCACACACATAACAGGACACCAGAAAA

CTTCCCCTGCAAAAATTTGGATGAAAACTACTGCCGCAATCCTGACGGAA

AAAGGGCCCCATGGTGCCATACAACCAACAGCCAAGTGCGGTGGGAGTAC

TGTAAGATACCGTCCTGTGACTCCTCCCCAGTATCCACGGAACAATTGGC

TCCCACAGCACCACCTGAGCTAACCCCTGTGGTCCAGGACTGCTACCATG

GTGATGGACAGAGCTACCGAGGCACATCCTCCACCACCACCACAGGAAAG

AAGTGTCAGTCTTGGTCATCTATGACACCACACCGGCACCAGAAGACCCC

AGAAAACTACCCAAATGCTGGCCTGACAATGAACTACTGCAGGAATCCAG

ATGCCGATAAAGGCCCCTGGTGTTTTACCACAGACCCCAGCGTCAGGTGG

GAGTACTGCAACCTGAAAAAATGCTCAGGAACAGAAGCGAGTGTTGTAGC

ACCTCCGCCTGTTGTCCTGCTTCCAGATGTAGAGACTCCTTCCGAAGAAG

ACTGTATGTTTGGGAATGGGAAAGGATACCGAGGCAAGAGGGCGACCACT

GTTACTGGGACGCCATGCCAGGACTGGGCTGCCCAGGAGCCCCATAGACA

CAGCATTTTCACTCCAGAGACAAATCCACGGGCGGGTCTGGAAAAAAATT

ACTGCCGTAACCCTGATGGTGATGTAGGTGGTCCCTGGTGCTACACGACA

AATCCAAGAAAACTTTACGACTACTGTGATGTCCCTCAGTGTGCGGCCCC

TTCATTTGATTGTGGGAAGCCTCAAGTGGAGCCGAAGAAATGTCCTGGAA

GGGTTGTAGGGGGGTGTGTGGCCCACCCACATTCCTGGCCCTGGCAAGTC

AGTCTTAGAACAAGGTTTGGAATGCACTTCTGTGGAGGCACCTTGATATC

CCCAGAGTGGGTGTTGACTGCTGCCCACTGCTTGGAGAAGTCCCCAAGGC

CTTCATCCTACAAGGTCATCCTGGGTGCACACCAAGAAGTGAATCTCGAA

CCGCATGTTCAGGAAATAGAAGTGTCTAGGCTGTTCTTGGAGCCCACACG

AAAAGATATTGCCTTGCTAAAGCTAAGCAGTCCTGCCGTCATCACTGACA

AAGTAATCCCAGCTTGTCTGCCATCCCCAAATTATGTGGTCGCTGACCGG

ACCGAATGTTTCATCACTGGCTGGGGAGAAACCCAAGGTACTTTTGGAGC

TGGCCTTCTCAAGGAAGCCCAGCTCCCTGTGATTGAGAATAAAGTGTGCA

ATCGCTATGAGTTTCTGAATGGAAGAGTCCAATCCACCGAACTCTGTGCT

GGGCATTTGGCCGGAGGCACTGACAGTTGCCAGGGTGACAGTGGAGGTCC

TCTGGTTTGCTTCGAGAAGGACAAATACATTTTACAAGGAGTCACTTCTT

GGGGTCTTGGCTGTGCACGCCCCAATAAGCCTGGTGTCTATGTTCGTGTT

TCAAGGTTTGTTACTTGGATTGAGGGAGTGATGAGAAATAATTAATTGGA

CGGGAGACAGAGTGACGCACTGACTCACCTAGAGGCTGGAACGTGGGTAG

GGATTTAGCATGCTGGAAATAACTGGCAGTAATCAAACGAAGACACTGTC

CCCAGCTACCAGCTACGCCAAACCTCGGCATTTTTTGTGTTATTTTCTGA

CTGCTGGATTCTGTAGTAAGGTGACATAGCTATGACATTTGTTAAAAATA

AACTCTGTACTTAACTTTGATTTGAGTAAATTTTGGTTTTGGTCTTCAAC

ATTTTCATGCTCTTTGTTCACCCCACCAATTTTTAAATGGGCAGATGGGG

GGATTTAGCTGCTTTTGATAAGGAACAGCTGCACAAAGGACTGAGCAGGC

TGCAAGGTCACAGAGGGGAGAGCCAAGAAGTTGTCCACGCATTTACCTCA

TCAGCTAACGAGGGCTTGACATGCATTTTTACTGTCTTTATTCCTGACAC

TGAGATGAATGTTTTCAAAGCTGCAACATGTATGGGGAGTCATGCAAACC

GATTCTGTTATTGGGAATGAAATCTGTCACCGACTGCTTGACTTGAGCCC

AGGGGACACGGAGCAGAGAGCTGTATATGATGGAGTGAACCGGTCCATGG

ATGTGTAACACAAGACCAACTGAGAGTCTGAATGTTATTCTGGGGCACAC

GTGAGTCTAGGATTGGTGCCAAGAGCATGTAAATGAACAACAAGCAAATA

TTGAAGGTGGACCACTTATTTCCCATTGCTAATTGCCTGCCCGGTTTTGA

AACAGTCTGCAGTACACACGGTCACAGGAGAATGACCTGTGGGAGAGATA

CATGTTTAGAAGGAAGAGAAAGGACAAAGGCACACGTTTTACCATTTAAA

ATATTGTTACCAAACAAAAATATCCATTCAAAATACAATTTAACAATGCA

ACAGTCATCTTACAGCAGAGAAATGCAGAGAAAAGCAAAACTGCAAGTGA

CTGTGAATAAAGGGTGAATGTAGTCTCAAATCCTCAAA
```

The signal peptide sequence of plasminogen is 19 amino acids long. Thus, the plasminogen sequence without the signal peptide encompasses amino acids from positions 20-810 of the plasminogen sequence. The signal peptide sequence is as follows: MEHKEVVLLLLLFLKSGQG (SEQ ID NO:3)

The plasmin heavy chain A is 561 amino acids, comprising the amino acid sequence provided below:

(SEQ ID NO: 4)
EPLDDYVNTQGASLFSVTKKQLGAGSIEECAAKCEEDEEFTCRAFQYHSK

EQQCVIMAENRKSSIIIRMRDVVLFEKKVYLSECKTGNGKNYRGTMSKTK

NGITCQKWSSTSPHRPRFSPATHPSEGLEENYCRNPDNDPQGPWCYTTDP

EKRYDYCDILECEEECMHCSGENYDGKISKTMSGLECQAWDSQSPHAHGY

IPSKFPNKNLKKNYCRNPDRELRPWCFTTDPNKRWELCDIPRCTTPPPSS

GPTYQCLKGTGENYRGNVAVTVSGHTCQHWSAQTPHTHNRTPENFPCKNL

DENYCRNPDGKRAPWCHTTNSQVRWEYCKIPSCDSSPVSTEQLAPTAPPE

LTPVVQDCYHGDGQSYRGTSSTTTTGKKCQSWSSMTPHRHQKTPENYPNA

-continued
GLTMNYCRNPDADKGPWCFTTDPSVRWEYCNLKKCSGTEASVVAPPPVVL

LPDVETPSEEDCMFGNGKGYRGKRATTVTGTPCQDWAAQEPHRHSIFTPE

TNPRAGLEKNYCRNPDGDVGGPWCYTTNPRKLYDYCDVPQCAAPSFDCGK

PQVEPKKCPGR

The short form of the plasmin heavy chain A is 483 amino acids. The amino acid sequence of the short form of the plasmin heavy chain A is as follows:

(SEQ ID NO: 5)
VYLSECKTGNGKNYRGTMSKTKNGITCQKWSSTSPHRPRFSPATHPSEGL

EENYCRNPDNDPQGPWCYTTDPEKRYDYCDILECEEECMHCSGENYDGKI

SKTMSGLECQAWDSQSPHAHGYIPSKFPNKNLKKNYCRNPDRELRPWCFT

TDPNKRWELCDIPRCTTPPPSSGPTYQCLKGTGENYRGNVAVTVSGHTCQ

HWSAQTPHTHNRTPENFPCKNLDENYCRNPDGKRAPWCHTTNSQVRWEYC

KIPSCDSSPVSTEQLAPTAPPELTPVVQDCYHGDGQSYRGTSSTTTTGKK

CQSWSSMTPHRHQKTPENYPNAGLTMNYCRNPDADKGPWCFTTDPSVRWE

YCNLKKCSGTEASVVAPPPVVLLPDVETPSEEDCMFGNGKGYRGKRATTV

TGTPCQDWAAQEPHRHSIFTPETNPRAGLEKNYCRNPDGDVGGPWCYTTN

PRKLYDYCDVPQCAAPSFDCGKPQVEPKKCPGR

The amino acid sequence of the activation peptide comprises the following amino acid sequence:

(SEQ ID NO: 6)
EPLDDYVNTQGASLFSVTKKQLGAGSIEECAAKCEEDEEFTCRAFQYHSK

EQQCVIMAENRKSSIIIRMRDVVLFEKK

The plasmin light chain B is 230 amino acids. The amino acid sequence of the plasmin light chain B is as follows:

(SEQ ID NO: 7)
VVGGCVAHPHSWPWQVSLRTRFGMHFCGGTLISPEWVLTAAHCLEKSPRP

SSYKVILGAHQEVNLEPHVQEIEVSRLFLEPTRKDIALLKLSSPAVITDK

VIPACLPSPNYVVADRTECFITGWGETQGTFGAGLLKEAQLPVIENKVCN

RYEFLNGRVQSTELCAGHLAGGTDSCQGDSGGPLVCFEKDKYILQGVTSW

GLGCARPNKPGVYVRVSRFVTWIEGVMRNN

In some preferred embodiments, the plasmin can be a miniplasmin or a microplasmin or a derivative thereof. Miniplasmin and microplasmin are produced upon the activation of miniplasminogen and microplasminogen by plasminogen activators such as, but not limited to, streptokinase, staphylokinase, tissue-type plasminogen activator or urokinase. Miniplasmin and microplasmin are derived from plasminogen, which is a single chain glycoprotein that is an important component of mammalian blood. Human plasminogen is a multi-domain protein of 791 residues (SEQ ID NO:1), composed of an N-terminal pre-activation domain, five homologous kringle domains each of about 80 amino acids, a serine protease catalytic domain and inter-domain connecting sequences. Plasmin or plasminogen activators cleave the peptide bonds between Arg-68 and Met-69, or Lys-77 and Lys-78 or Lys-78 and Val-79 at the N-terminal of human plasminogen, resulting in shorter proenzymes called Lys-plasminogens (for example, proteins consisting of amino acids 69-791 or 78-791 or 79-791). Additional cleavage by the enzyme elastase removes the first four kringle domains producing the proenzyme, miniplasminogen (typically amino acids 442-791). Further cleavage of the fifth kringle yields the proenzyme, microplasminogen (typically amino acids 543-791). The kringles of plasminogen contain lysine-binding sites that mediate specific binding of plasminogen to substrates such as fibrin. The proenzyme forms of plasminogen are activated to their enzymatically active form by the cleavage of the peptide bond between Arg-561 and Val-562 to yield a disulfide bonded double chain form of the corresponding protein. The product of activation of a plasminogen protein is called a plasmin. Thus, the product of Lys-plasminogen activation is called Lys-plasmin, while the products of activation of miniplasminogen and microplasminogen, are referred to as miniplasmin and microplasmin, respectively. Like plasmin, miniplasmin and microplasmin possess catalytic activity. An advantage of miniplasmin and microplasmin over plasmin is their smaller size compared to plasmin. Thus, both microplasmin and miniplasmin are expected to have faster diffusion rates in the vitreous than plasmin.

The plasmin of the present invention may comprise any one of the plasminogen-related sequences described herein, for example, any one of SEQ ID NOs: 1 and 3-7, or a functional fragment or variant thereof.

The plasmin may also be ocriplasmin (JETREA®) or variants or derivatives thereof. Ocriplasmin is a recombinant truncated form of human plasmin produced by recombinant DNA technology in a *Pichia pastoris* expression system. Ocriplasm is a protein made up of 249 amino acids with a molecular weight of 27.2 kDa, and has two peptide chains. The amino acid sequence for the truncated heavy chain is as follows:

APSFDCGKPQVEPKKCPGR       (SEQ ID NO: 8)

The amino acid sequence for the light chain is as follows:

(SEQ ID NO: 9)
VVGGCVAHPHSWPWQVSLRTRFGMHFCGGTLISPEWVLTAAHCLEKSPRP

SSYKVILGAHQEVNLEPHVQEIEVSRLFLEPTRKDIALLKLSSPAVITDK

VIPACLPSPNYVVADRTECFITGWGETQGTFGAGLLKEAQLPVIENKVCN

RYEFLNGRVQSTELCAGHLAGGTDSCQGDSGGPLVCFEKDKYILQGVTSW

GLGCARPNKPGVYVRVSRFVTWIEGVMRNN

The present invention further encompasses variants and derivatives of ocriplasmin.

The plasmin may be isolated from blood using known isolation techniques. Alternatively, plasminogen may be isolated from the blood using known isolation techniques, and then incubated with proteases that cleave plasminogen into active plasmin to produce purified or isolated plasmin suitable for use in the methods described herein.

The plasmin may be synthesized chemically using commercially available peptide synthesizers to produce purified or isolated plasmin suitable for use in the methods described herein. Chemical synthesis of peptides and proteins can be used for the incorporation of modified or unnatural amino acids, including D-amino acids and other small organic molecules. Replacement of one or more L-amino acids in a peptide or protein with the corresponding D-amino acid isoforms can be used to increase resistance to enzymatic hydrolysis, and to enhance one or more properties of biological activity, i.e., functional potency or duration of action. Other modifications to the plasmin can be introduced, for example, cross-linking to change the conformation to alter the potency, selectivity or stability of the plasmin.

For example, the plasmin may be purchased from a commercial vendor, such as Sigma Aldrich, Catalog Number P1867. The present invention also encompasses variants or derivatives of the plasmin supplied by Sigma Aldrich (Cat. No. P1867).

The plasmin may be a recombinant plasmin obtained by methods well known in the art for recombinant protein expression and purification. A DNA molecule encoding a plasmin or a variant or analog thereof can be generated from known DNA sequences or by deducing the nucleic acid sequences from the amino acid sequence based on known codon usage. The DNA molecule encoding a plasmin can be cloned into a suitable vector, such as a cloning or expression vector, by any of the methodologies known in the art. The cloning or expression vectors contain all the components required for additional cloning of the plasmin DNA, such as restriction enzyme sites, or for the expression of the plasmin, such as a host-specific promoter, and optionally, enhancer sequences. The expression vector can be introduced and expressed in a host cell. A host cell can be any prokaryotic or eukaryotic cell. For example, the plasmin can be expressed in bacterial cells (i.e., $E.$ $coli$), yeast, insect cells (i.e., Sf9), or mammalian cells. Other suitable host cells are known to those skilled in the art. The host cell can be used to produce or overexpress the plasmin, variant or derivative thereof in culture. Then the biologically expressed plasmin, variant or derivative thereof may be purified using known purification techniques, such as affinity chromatography, to produce purified or isolated plasmin suitable for use in the methods described herein.

In some embodiments, a variant, derivative or analog of a plasmin may be preferred. Variants, derivatives and analogs of plasmin can be identified or generated by one ordinarily skilled in the art. The plasmin variants, derivatives and analogs can be generated, for example, by using the recombinant methods or methods of synthesis described herein. Plasmin derivatives known in the art include miniplasmin and microplasmin are also suitable for use in the methods disclosed herein.

As used herein, the term "derivative" and "variant" may be used interchangeably and refers to a plasmin that differs from naturally occurring plasmin, but retains the essential properties thereof. For example, the plasmin derivative may be a biologically active fragment of plasmin, for example, a truncated plasmin. The biologically active fragment contains the catalytic domain of plasmin and possesses serine protease catalytic activity. Alternatively, the plasmin derivative may be a mutated plasmin, wherein at least 1 amino acid, at least 2, at least 3, at least 4, at least 5, at least 6, at least 7, at least 8, at least 9, at least 10, at least 20, at least 30, at least 40, or at least 50 amino acids are mutated from the wild-type plasmin. Mutated plasmin may have altered sequences by substitutions, additions, or deletions, that still result in functionally equivalent molecules. In one embodiment, the plasmin derivative is about 99%, about 98%, about 97%, about 96%, about 95%, about 90%, about 85%, about 80%, about 75%, about 70%, about 65%, about 60%, about 55%, or about 50% identity to wild-type plasmin. In some instances, the mutation may increase the potency (protease activity), stability, or number of targets of the plasmin. In another aspect, the mutation may decrease the potency, stability, or number of targets of the plasmin. The mutation may be a conservative amino acid substitution. Alternatively, the mutation may be a non-conservative amino acid substitution. In another embodiment, the plasmin derivative may be chemically modified, for example, by the addition of a chemical moiety that alters activity or stability.

The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using search algorithms such as BLAST and PSI-BLAST (Altschul et al., 1990, J Mol Biol 215:3, 403-410; Altschul et al., 1997, Nucleic Acids Res 25:17, 3389-402).

The term "analog" as used herein refers to compounds or peptides that retain the essential protease activity of the plasmin. For example, the analog may bear some amino acid sequence similarity to or no sequence similarity to naturally occurring plasmin. However all plasmin analogs retain the functional capability of protease cleavage of any one of the targets of plasmin (i.e., laminin, fibrin), and/or the preferential cleavage at the carboxyl side of Lysine and Arginine residues.

Plasmin derivatives and analogs can be identified by one ordinarily skilled in the art by screening combinatorial libraries of mutants of plasmin or general therapeutic or pharmaceutical compounds.

Methods of Use

The present invention provides methods for enhancing the delivery of a therapeutic agent to the eye. The methods of the present invention include administering a plasmin and a therapeutic agent to the eye. The therapeutic agent may be delivered to the eye by any method known in the art. Routes of administration include, but are not limited to, intravitreal, intracameral, subconjunctival, subtenon, retrobulbar, posterior juxtascleral, or topical. Delivery methods include, for example, injection by a syringe and a drug delivery device, such as an implanted vitreal delivery device (i.e., VITRASERT®).

Preferably, the therapeutic agent is administered to the vitreous by intravitreal injection for delivery of therapeutic agents to the retina. In some embodiments, the methods of the present invention provide enhanced delivery to cells of the retina. Exemplary retinal cells, include, but are not limited to, photoreceptor cells (e.g., rods, cones, and photosensitive retinal ganglion cells), horizontal cells, bipolar cells, amacrine cells, retinal ganglion cells, Müller glial cell, and retinal pigment epithelial cells.

In one embodiment, the plasmin or derivative thereof is administered concurrently or sequentially with the therapeutic agent. For concurrent administration, the plasmin or derivative thereof can be formulated with the therapeutic agent in a single composition suitable for delivery, for example, injection, by methods known in the art. Alternatively, the plasmin or derivative thereof can be injected in separate compositions, simultaneously or sequentially. In a preferred embodiment, the plasmin may be administered prior to administration of the therapeutic agent.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, A E., *Remington: The Science and Practice of Pharmacy*, Lippincott Williams & Wilkins Publishers; 2003 or latest edition). See also, WO00/15822. If the preparation is to be stored for long periods, it may be frozen, for example, in the presence of glycerol.

The dosage of plasmin or derivative thereof to be administered can be optimized by one of ordinary skill in the art. Delivery to certain target ocular tissues may require lower doses of plasmin or higher doses of plasmin, depending on the location of the target tissue, intervening ocular structures, and ability of the agent to penetrate the target tissue. Preferably, the dose of plasmin administered is about 0.001 UI (enzyme units) per eye, 0.025 UI per eye, about 0.05 UI per eye, about 0.075 UI per eye, about 0.100 UI per eye, about 0.150 UI per eye, or about 0.200 UI per eye.

In some embodiments, the methods for enhanced delivery disclosed herein may provide increased efficacy of a therapeutic agent. Increased efficacy of the therapeutic agent can be determined by measuring the therapeutic effect of the therapeutic agent. Treatment is efficacious if the treatment leads to clinical benefit such as, alleviation of a symptom in the subject. For example, in a degenerative retinal disease, such as retinitis pigmentosa, treatment is efficacious when light sensitivity or another aspect of vision is improved or restored. When treatment is applied prophylactically, "efficacious" means that the treatment retards or prevents an ocular disease or disorder or prevents or alleviates a symptom of clinical symptom of an ocular disease or disorder. Efficaciousness is determined in association with any known method for diagnosing or treating the particular ocular disease or disorder.

In some embodiments, the therapeutic agent is a nucleic acid or a nucleic acid expression vector (i.e. a viral vector) encoding a therapeutic transgene or an siRNA species (i.e., short hairpin or microRNA). With regard to such therapeutic agents, the enhanced delivery of a therapeutic agent provided by the methods disclosed herein may result in increased transduction efficiency. Increased transduction efficiency can be determined by measuring the level of expression of the transgene introduced by the viral vector.

Therapeutic Agents

The therapeutic agents to be delivered to the eye by the methods described herein are any therapeutic agents known in the art for treating, alleviating, reducing, or preventing a symptom of an ocular disease, an ocular disorder, or an ocular condition. The therapeutic agent may be a small molecule, a nucleic acid, an antibody, or a peptide.

Examples of small molecules suitable for use in the methods described herein include, but are not limited to, tyrosine kinase inhibitors, antibiotics, anti-inflammatory agents, glucocorticoids, opioid antagonists, and other enzyme inhibitors.

Examples of nucleic acids suitable for use in the methods described herein include, but are not limited to, viral vectors encoding therapeutic transgenes (i.e., channelopsins, or halorhodopsin), RNA interference molecules (i.e., short hairpins, siRNA, or microRNAs). In a particularly preferred embodiment, the therapeutic agents are viral vectors encoding transgenes for gene therapy. Particularly preferred viral vectors are rAAV vectors that encode channelopsins or halorhodopsins for expression in the retina to restore light sensitivity.

Examples of antibodies suitable for use in the methods described herein include, but are not limited to, ranibizumab (Lucentis®), VEGF antibodies (Eylea®), bevacizumab (Avastin®), infliximab, etanercept, and adalimumab.

Examples of proteins or peptides suitable for use in the methods described herein include, but are no limited to, microplasmin (Ocriplasmin, Jetrea®), macugen pagylated polypeptide (Pegaptanib), and integrin peptides. In some aspects, the peptide therapeutic is a collection of peptides, containing two or more peptides.

Any of the therapeutic agents described herein may be optionally encapsulated in a carrier, such as a nanoparticle, a polymer, or a liposome. These carrier agents may serve to further enhance the delivery of the therapeutic agent to the eye. In some aspects, the carrier agents may alter the properties of the therapeutic agents, such as increasing the stability (half-life) or providing sustained-release properties to the therapeutic agents. Alternatively, the carrier may protect the therapeutic agent from the proteolytic activities of plasmin if formulated in the same composition for delivery.

Gene Therapy

As a large number of ocular diseases and disorders result from aberrant gene expression in various ocular tissues, gene therapy possesses increasing potential as an effective therapy. However, the efficacy of gene therapy in the eye has been limited due to the challenges of effective delivery and transduction of the therapeutic viral vectors throughout any ocular tissue.

Thus, the present invention provides methods for increased efficiency of delivery of transgenes to the eye for treating an ocular disease or disorder, or for restoring or improving vision. Transgenes of particular interest for restoration of photosensitivity or vision include photosensitive proteins, such as opsin genes or rhodopsin genes. As used herein, "transgene" refers to a polynucleotide encoding a polypeptide of interest, wherein the polynucleotide is present in a nucleic acid expression vector suitable for gene therapy (e.g., a viral vector such as AAV).

Previous studies have shown that injection of a recombinant adeno-associated viral vector encoding a transgene, such as channelopsin-2, results in poor delivery of the vector and low expression of Chop2 in the inner retinal cells, especially bipolar cells. In non-human primates, AAV-mediated gene transfection was found to be more efficient in peripheral retina, fovea, and along blood vessels, suggesting that inner limiting membrane (ILM), which is the boundary between the retina and the vitreous space, is a major barrier (Ivanova et al., 2010).

The present invention provides a solution to this problem by using plasmin or derivatives thereof to dissolve the components the ILM, such as laminin and fibronectin. Accordingly, therapeutic agents will have greater accessibility to the retina, specifically the cells of the inner retina such as the retinal bipolar cells, retinal ganglion cells, Müller glial cells, and retinal pigment epithelial cells. The methods described herein provide enhanced delivery of therapeutic compounds, such as therapeutic viral vectors. The enhanced delivery of viral vectors is demonstrated by increased transduction efficiency, increased expression of the therapeutic transgene (i.e., Chop2), and increased efficacy of the therapeutic compound (i.e., increased light sensitivity or restoration of vision).

Nucleic acid expression vectors suitable for use in gene therapy are known in the art. For example, the nucleic acid expression vector is a viral vector. The viral vectors can be retroviral vectors, adenoviral vectors, adeno-associated vectors (AAV), or lentiviral vectors, or any engineered or recombinant viral vector known in the art. Particularly preferred viral vectors are adeno-associated vectors, for example, AAV-1, AAV-2, AAV-3, AAV-4, AAV-5, AAV-6, AAV-7, AAV-8, AAV-9, AAV-10, AAV-11, AAV-12 or any engineered or recombinant AAV known in the art. In a particularly preferred embodiment, the vector is recombinant AAV-2 (rAAV2).

In some embodiments, a recombinant adeno-associated viral (rAAV) vector comprises a capsid protein with a mutated tyrosine residue which enables to the vector to have improved transduction efficiency of a target cell, e.g., a retinal bipolar cell (e.g. ON or OFF retinal bipolar cells; rod and cone bipolar cells). In some cases, the rAAV further comprises a promoter (e.g., mGluR6, or fragment thereof) capable of driving the expression of a protein of interest in the target cell.

In one embodiment, a mutation may be made in any one or more of tyrosine residues of the capsid protein of AAV 1-12 or hybrid AAVs. In specific embodiments these are surface exposed tyrosine residues. In a related embodiment the tyrosine residues are part of the VP1, VP2, or VP3 capsid protein. In exemplary embodiments, the mutation may be made at one or more of the following amino acid residues of an AAV-VP3 capsid protein: Tyr252, Tyr272, Tyr444, Tyr500, Tyr700, Tyr704, Tyr730; Tyr275, Tyr281, Tyr508, Tyr576, Tyr673 or Tyr720. Exemplary mutations are tyrosine-to-phenylalanine mutations including, but not limited to, Y252F, Y272F, Y444F, Y500F, Y700F, Y704F, Y730F, Y275F, Y281F, Y508F, Y576F, Y612G, Y673F and Y720F. In a specific embodiment these mutations are made in the AAV2 serotype. In some cases, an AAV2 serotype comprises a Y444F mutation and/or an AAV8 serotype comprises a Y733F mutation, wherein 444 and 733 indicate the location of a point tyrosine mutation of the viral capsid. In further embodiments, such mutated AAV2 and AAV8 serotypes encode a light-sensitive protein and also comprise a modified mGluR6 promoter to drive expression of such light-sensitive protein. Such AAV vectors are described in, for example, Petrs-Silva et al, Mol Ther., 2011 19:293-301).

In some embodiments, the expression of the therapeutic transgene is driven by a constitutive promoter, i.e., CAG promoter, CMV promoter, LTR. In other embodiments, the promoter is an inducible or a cell-specific promoter. Cell type-specific promoters that enable transgene expression in specific subpopulations of cells, i.e., retinal neuron cells or degenerating cells, may be preferred. These cells may include, but are not limited to, a retinal ganglion cell, a photoreceptor cell, a bipolar cell, a rod bipolar cell, an ON-type cone bipolar cell, a retinal ganglion cell, a photosensitive retinal ganglion cell, a horizontal cell, an amacrine cell, an AII amacrine cell, or a retinal pigment epithelial cell. Cell type-specific promoters are well known in the art. Particularly preferred cell type-specific promoters include, but are not limited to mGluR6, NK-3, and Pcp2(L7). Cell type-specific promoters modified using recombinant DNA techniques known in the art to increase efficiency of expression and selective targeting are also encompassed in the present invention. For example, a modified mGluR6 promoter contains a combination of regulatory elements from the mGluR6 gene, as described in U.S. Provisional Application No. 61/951,360, hereby incorporated by reference in its entirety.

In one embodiment of the present invention, the therapeutic transgene can be any light-sensitive opsin. The opsin family of genes includes vertebrate (animal) and invertebrate opsins. Animal opsins are G-protein coupled receptors (GPCRs) with 7-transmembrane helices which regulate the activity of ion channels. Invetertebrate rhodopsins are usually not GPCRs but are light-sensitive or light-activated ion pumps or ion channels.

As referred to herein, an opsin gene or light-sensitive protein includes, but is not limited to, channelrhodopsins, or channelopsins, (i.e., ChR1, ChR2, vChR1 from *Volvox carteri*, vChR2, and other variants identified from any vertebrate, invertebrate, or microbe), halorhodopsins (NpHR), melanopsins, pineal opsins, photopsins, bacteriorhodopsins, proteorhodopsins and functional variants or chimeras thereof. A light-sensitive protein of this invention can occur naturally in plant, animal, archaebacterial, algal, or bacterial cells, or can alternatively be created through laboratory techniques. Examples of opsin genes are discussed in further detail below.

Examples of channelrhodopsins, or channelopsins, as transgenes in the present invention include channelrhodopsins Chop1 (also known as ChR1) (GenBank accession number AB058890/AF385748) and Chop2 (also known as ChR2) (GenBank accession number AB058891/AF461397) are two rhodopsins from the green alga *Chlamydomonas reinhardtii* (Nagel, 2002; Nagel, 2003). Channelopsins are a seven transmembrane domain proteins that become photoswitchable (light sensitive) when bound to the chromophore all-trans-retinal. Channelopsins, when linked to a retinal molecule via Schiff base linkage forms a light-gated, non-specific, inwardly rectifying, cation channel, called a channelrhodopsin. These light-sensitive channels that, when expressed and activated in neural tissue, allow for a cell to be depolarized when stimulated with light (Boyden, 2005). A Chop2 fragment (315 amino acids) has been shown to efficiently increase photosensitivity and vision in mouse models of photoreceptor degeneration (Bi et al., Neuron, 2006, and U.S. Pat. No. 8,470,790; both of which are hereby incorporated by reference). Chop2 mutants and variants as described in PCT Publication WO 2013/134295 (hereby incorporated by reference) may also be expressed using the promoters described herein. The present invention also provides for use of *Volvox carteri* channelrhodopsins (i.e., vChR1 and vChR2).

NpHR (Halorhodopsin) (GenBank accession number EF474018) is from the haloalkaliphilic archaeon *Natronomonas pharaonis*. In certain embodiments variants of NpHR can be created. In specific embodiments single or multiple point mutations to the NpHR protein can result in NpHR variants. In specific embodiments a mammalian codon optimized version of NpHR can be utilized. In one embodiment NpHR variants are utilized. In one specific embodiment eNpHR (enhanced NpHR) is utilized. Addition of the amino acids FCYENEV to the NpHR C-terminus along with the signal peptide from the β subunit of the nicotinic acetylcholine receptor to the NpHR N-terminus results in the construction of eNpHR.

Melanopsin (GenBank accession number 6693702) is a photopigment found in specialized photosensitive ganglion cells of the retina that are involved in the regulation of circadian rhythms, pupillary light reflex, and other non-visual responses to light. In structure, melanopsin is an opsin, a retinylidene protein variety of G-protein-coupled receptor. Melanopsin resembles invertebrate opsins in many respects, including its amino acid sequence and downstream signaling cascade. Like invertebrate opsins, melanopsin appears to be a bistable photopigment, with intrinsic photoisomerase activity. In certain embodiments variants of melanopsin can be created. In specific embodiments single or multiple point mutations to the melanopsin protein can result in melanopsin variants.

Light-sensitive proteins may also include proteins that are at least about 10%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95%, or at least about 99% identical to any of the light-sensitive proteins described herein (i.e., ChR1, ChR2, vChR1, vChR2, NpHR and melanopsin). The light-sensitive proteins of the present invention may also include proteins that have at least one mutation. The mutation may be a point mutation.

In some embodiments, light-sensitive proteins can modulate signaling within neural circuits and bidirectionally control behavior of ionic conductance at the level of a single neuron. In some embodiments the neuron is a retinal neuron, a retinal bipolar cell (e.g. ON or OFF retinal bipolar cells; rod and cone bipolar cells), a retinal ganglion cell, a photoreceptor cell, or a retinal amacrine cell.

In some embodiments, a polyA tail can be inserted downstream of the transgene in an expression cassette or nucleic acid expression vector of the present invention. Suitable polyA tails are known in the art, and include, for example, human growth hormone poly A tail (hGHpA), bovine growth hormone polyA tail (bGHpA), bovine polyA, SV40 polyA, and AV40pA.

Upon illumination by the preferred dose of light radiation, rhodopsin proteins opens the pore of the channel, through which $H^+$, $Na^+$, $K^+$, and/or $Ca^{2+}$ ions flow into the cell from the extracellular space. Activation of the rhodopsin channel typically causes a depolarization of the cell expressing the channel. Depolarized cells produce graded potentials and or action potentials to carry information from the rhodopsin-expressing cell to other cells of the retina or brain, to increase light sensitivity or restore vision. Methods of improving vision or light sensitivity by administration of a vector encoding a channelopsin (or variant thereof) are described in PCT/US2007/068263, the contents of which are herein incorporated in its entirety.

Accordingly, a dual rhodopsin system can be used to recapitulate the ON and OFF pathways integral to visual processing and acuity. Briefly, a Chop2 protein of the present invention can be specifically targeted to ON type retinal neurons (i.e., ON type ganglion cells and/or ON type bipolar cells), while a hypopolarizing light sensor (i.e., halorhodopsin or other chloride pump known in the art) can be targeted to OFF type retinal neurons (i.e. OFF type ganglion cells and/or OFF type bipolar cells) to create ON and OFF pathways. The specific targeting to preferred cell subpopulations can be achieved through the use of different cell type-specific promoters. For example, Chop2 expression may be driven by the mGluR6 promoter for targeted expression in ON-type retinal neurons (i.e., ON type ganglion cells and/or ON type bipolar cells) while a hypopolarizing channel, such as halorhodopsin, expression is driven by the NK-3 promoter for targeted expression in OFF-type retinal neurons (i.e., OFF type ganglion cells and/or OFF type bipolar cells).

An alternative approach to restore ON and OFF pathways in the retina is achieved by, expressing a depolarizing light sensor, such as ChR2, to rod bipolar cells or AII amacrine. In this approach, the depolarization of rod bipolar cells or AII amacrine cells can lead to the ON and OFF responses at the levels of cone bipolar cells and the downstream retinal ganglion cells. Thus, the ON and OFF pathways that are inherent in the retina are maintained.

An effective amount of rAAV virions carrying a nucleic acid sequence encoding the rhodopsin DNA under the control of the promoter of choice, preferably a constitutive CMV promoter or a cell-specific promoter such as mGluR6, is preferably in the range of between about $10^{10}$ to about $10^{13}$ rAAV infectious units in a volume of between about 25 and about 800 μl per injection. The rAAV infectious units can be measured according to McLaughlin, S K et al., 1988, *J Virol* 62:1963. More preferably, the effective amount is between about $10^{10}$ and about $10^{12}$ rAAV infectious units and the injection volume is preferably between about 50 and about 150 μl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid(s) or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The ocular disorders for which the methods of the present invention are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. Other ocular diseases that may benefit from the methods described herein include, but are not limited to, retinoblastoma, ocular melanoma, diabetic retinopathy, hypertensive retinopathy, any inflammation of the ocular tissues (i.e., chorioretinal inflammation, scleritis, keratitis, uveitis, etc.), or infection (i.e., bacterial or viral).

In particular, the viral-mediated delivery of rhodopsins using the methods of the present invention useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by the methods described herein. Thus, the particular ocular disorder treated by the present invention may include the above-mentioned disorders and a number of diseases which have yet to be so characterized.

Restoration of Light Sensitivity

These methods described herein may be used in subjects of normal and/or impaired vision. The enhanced delivery of a therapeutic compound, as described herein, may preserve, improve, or restore vision. The term "vision" as used herein is defined as the ability of an organism to usefully detect light as a stimulus for differentiation or action. Vision is intended to encompass the following:
1. Light detection or perception—the ability to discern whether or not light is present;
2. Light projection—the ability to discern the direction from which a light stimulus is coming;
3. Resolution—the ability to detect differing brightness levels (i.e., contrast) in a grating or letter target; and
4. Recognition—the ability to recognize the shape of a visual target by reference to the differing contrast levels within the target.

Thus, "vision" includes the ability to simply detect the presence of light. The methods of the present invention can be used to improve or restore vision, wherein the improvement or restoration in vision includes, for example, increases in light detection or perception, increase in light sensitivity or photosensitivity in response to a light stimulus, increase in the ability to discern the direction from which a light stimulus is coming, increase in the ability to detect differing brightness levels, increase in the ability to recognize the shape of a visual target, and increases in visual evoked potential or transmission from the retina to the cortex. As such, improvement or restoration of vision may or may not include full restoration of sight, i.e., wherein the vision of the patient treated with the present invention is restored to the degree to the vision of a non-affected individual. The visual recovery described in the animal studies described below may, in human terms, place the person on the low end of vision function by increasing one aspect of vision (i.e., light sensitivity, or visual evoked potential) without restoring full sight. Nevertheless, placement at such a level would be a significant benefit because these individuals could be trained in mobility and potentially in low order resolution tasks which would provide them with a greatly improved level of visual independence compared to total blindness. Even basic light perception can be used by visually impaired individuals, whose vision is improved using the present compositions and methods, to accomplish specific daily tasks and improve general mobility, capability, and quality of life.

The degree of restoration of vision can be determined through the measurement of vision before, and preferably after, administering a vector comprising, for example, DNA encoding a therapeutic transgene such as Chop2 or halorhodopsin or both. Vision can be measured using any of a number of methods well-known in the art or methods not yet established. Vision, as improved or restored by the present invention, can be measured by any of the following visual responses:
1. a light detection response by the subject after exposure to a light stimulus—in which evidence is sought for a reliable response of an indication or movement in the general direction of the light by the subject individual when the light it is turned on;
2. a light projection response by the subject after exposure to a light stimulus in which evidence is sought for a reliable response of indication or movement in the specific direction of the light by the individual when the light is turned on;
3. light resolution by the subject of a light vs. dark patterned visual stimulus, which measures the subject's capability of resolving light vs dark patterned visual stimuli as evidenced by:
   a. the presence of demonstrable reliable optokinetically produced nystagmoid eye movements and/or related head or body movements that demonstrate tracking of the target (see above) and/or
   b. the presence of a reliable ability to discriminate a pattern visual stimulus and to indicate such discrimination by verbal or non-verbal means, including, for example pointing, or pressing a bar or a button; or
4. electrical recording of a visual cortex response to a light flash stimulus or a pattern visual stimulus, which is an endpoint of electrical transmission from a restored retina to the visual cortex, also referred to as the visual evoked potential (VEP). Measurement may be by electrical recording on the scalp surface at the region of the visual cortex, on the cortical surface, and/or recording within cells of the visual cortex.

Thus, improvement or restoration of vision, according to the present invention, can include, but is not limited to: increases in amplitude or kinetics of photocurents or electrical response in response to light stimulus in the retinal cells, increases in light sensitivity (i.e., lowering the threshold light intensity required for initiating a photocurrent or electrical response in response to light stimulus, thereby requiring less or lower light to evoke a photocurrent) of the retinal cells, increases in number or amplitude of light-evoked spiking or spike firings, increases in light responses to the visual cortex, which includes increasing in visual evoked potential transmitted from the retina or retinal cells to the visual cortex or the brain.

Both in vitro and in vivo studies to assess the various parameters of the present invention may be used, including recognized animal models of blinding human ocular disorders. Large animal models of human retinopathy, e.g., childhood blindness, are useful. The examples provided herein allow one of skill in the art to readily anticipate that this method may be similarly used in treating a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters.

Behavioral measures can be obtained using known animal models and tests, for example performance in a water maze, wherein a subject in whom vision has been preserved or restored to varying extents will swim toward light (Hayes, J M et al., 1993, *Behav Genet* 23:395-403).

In models in which blindness is induced during adult life or congenital blindness develops slowly enough that the individual experiences vision before losing it, training of the subject in various tests may be done. In this way, when these tests are re-administered after visual loss to test the efficacy of the present compositions and methods for their vision-restorative effects, animals do not have to learn the tasks de novo while in a blind state. Other behavioral tests do not require learning and rely on the instinctiveness of certain behaviors. An example is the optokinetic nystagmus test (Balkema G W et al., 1984, *Invest Ophthalmol Vis Sci.* 25:795-800; Mitchiner J C et al., 1976, *Vision Res.* 16:1169-71).

The present invention may also be used in combination with other forms of vision therapy known in the art to improve or restore vision. For example, the use of visual prostheses, which include retinal implants, cortical implants, lateral geniculate nucleus implants, or optic nerve implants. Thus, in addition to genetic modification of surviving retinal neurons using the present methods, the subject being treated may be provided with a visual prosthesis before, at the same time as, or after the molecular method is employed. The effectiveness of visual prosthetics can be improved with training of the individual, thus enhancing the potential impact of the Chop2 transformation of patient cells as contemplated herein. Training methods, such as habituation training characterized by training the subject to recognize recognize (i) varying levels of light and/or pattern stimulation, and/or (ii) environmental stimulation from a common light source or object as would be understood by one skilled in the art; and orientation and mobility training characterized by training the subject to detect visually local objects and move among said objects more effectively than without the training. In fact, any visual stimulation techniques that are typically used in the field of low vision rehabilitation are applicable here.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Preferably, the subject is a human. A "subject in need thereof" is a subject suffering from or at risk of developing or suffering from an ocular disease or disorder. A subject at risk of developing or suffering from an ocular disease or disorder can be diagnosed by a physician or ocular specialist using routine methods in the art.

EXAMPLES

Example 1

Plasmin Increases Delivery of AAV2-Vector Encoding Chop2 to the Retina

Delivery of a therapeutic viral construct encoding a functional GFP-channelopsin-2 protein to the retina was examined. Injection of $6 \times 10^{12}$ vg/ml of AAV2 vector AAV2/2-ChR2-GFP-WPRE-hGHpA in control (FIG. 1A) or co-injection with plasmin (FIG. 1B) was performed into the vitreous space of the eye of one month old C56BL/6J. The concentration of plasmin injected with vector was 0.0251 U/eye. After one month, the mice retinas were isolated, and retinal vertical sections were prepared. The sections were immunostained and cells were counted. Immunofluorescence analysis of the sections showed that co-injection with plasmin increased the transduction efficiency of the therapeutic AAV2-ChR2-GFP vector, as evidenced by increased fluorescence in comparison to control (FIG. 1).

Example 2

Plasmin Increases Transduction Efficiency in Retinal Ganglion Cells

Figure 2:
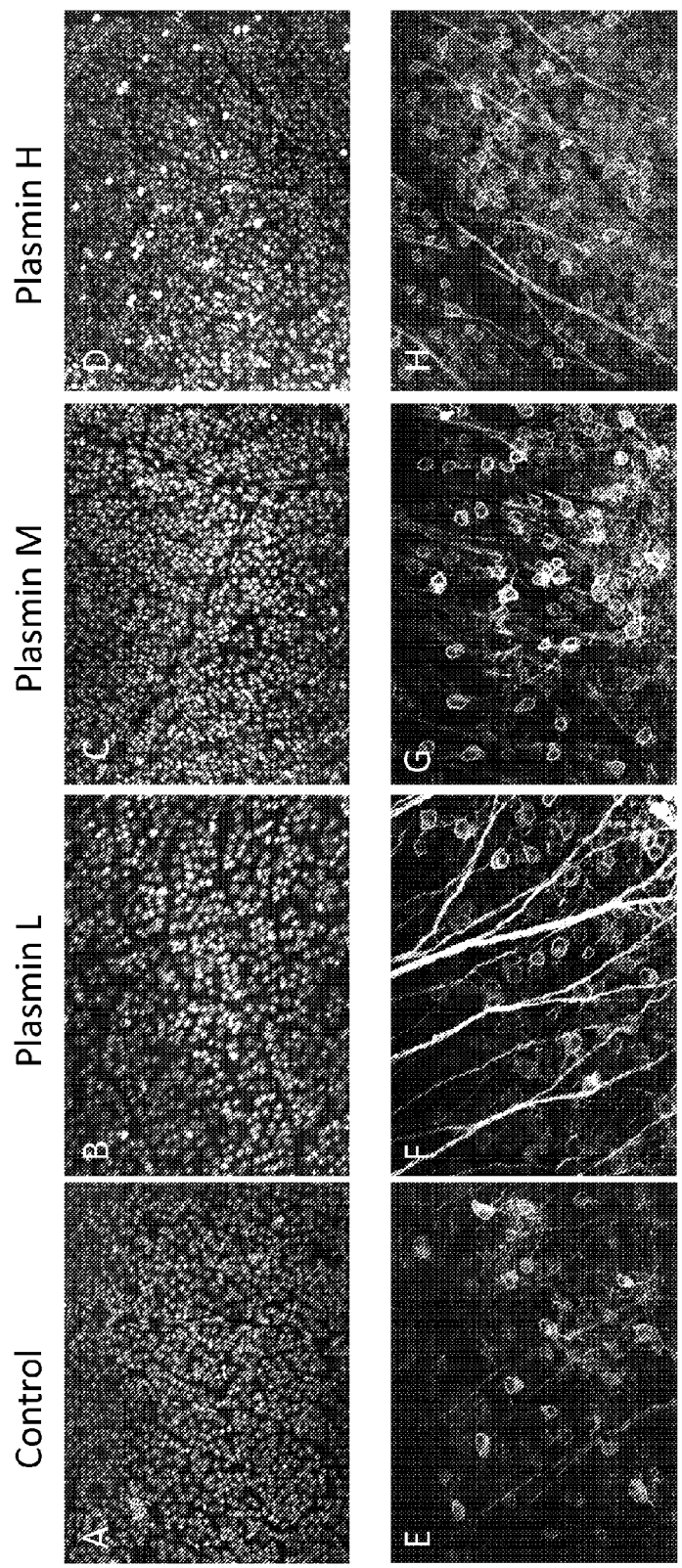
FIG. 2 is a series of representative GFP fluorescence and DAPI staining images demonstrating the effects of plasmin on AAV-mediated transduction efficiency and the potential neurotoxicity in retinal ganglion cells. AAV2 vectors ($2\times10^{12}$ vg/ml), AAV2/2-ChR2-GFP-WPRE-hGHpA, was injected in control (A, E), or was co-injected at (B, F) low (L: 0.005 IU), (C, G) middle (M: 0.0251U), and (D, H) high (H: 0.100 IU plasmin/eye) concentrations. Retinal ganglion cells were stained by DAPI (A-D).

Using the same experimental set-up as in Example 1, a vector ($2 \times 10^{12}$ vg/ml) encoding GFP was co-injected with either control or varying concentrations of plasmin: low (L=0.005 IU/eye), middle (M=0.0251 U/eye), and high (H=0.100 IU/eye). After 1 month, retinal whole mounts were prepared and immunostained. Representative images for each plasmin concentration and control are shown in FIG. 2. As shown, treatment with plasmin increases GFP expression.

To further quantify these results, GFP-expressing retinal ganglion cells were counted from multiple unit areas of 223 μm×167 μm. The results are presented in FIG. 3A. As shown, treatment with low, middle and high doses of plasmin resulted in statistically significantly increased levels of GFP expression in retinal ganglion cells.

Figure 3:
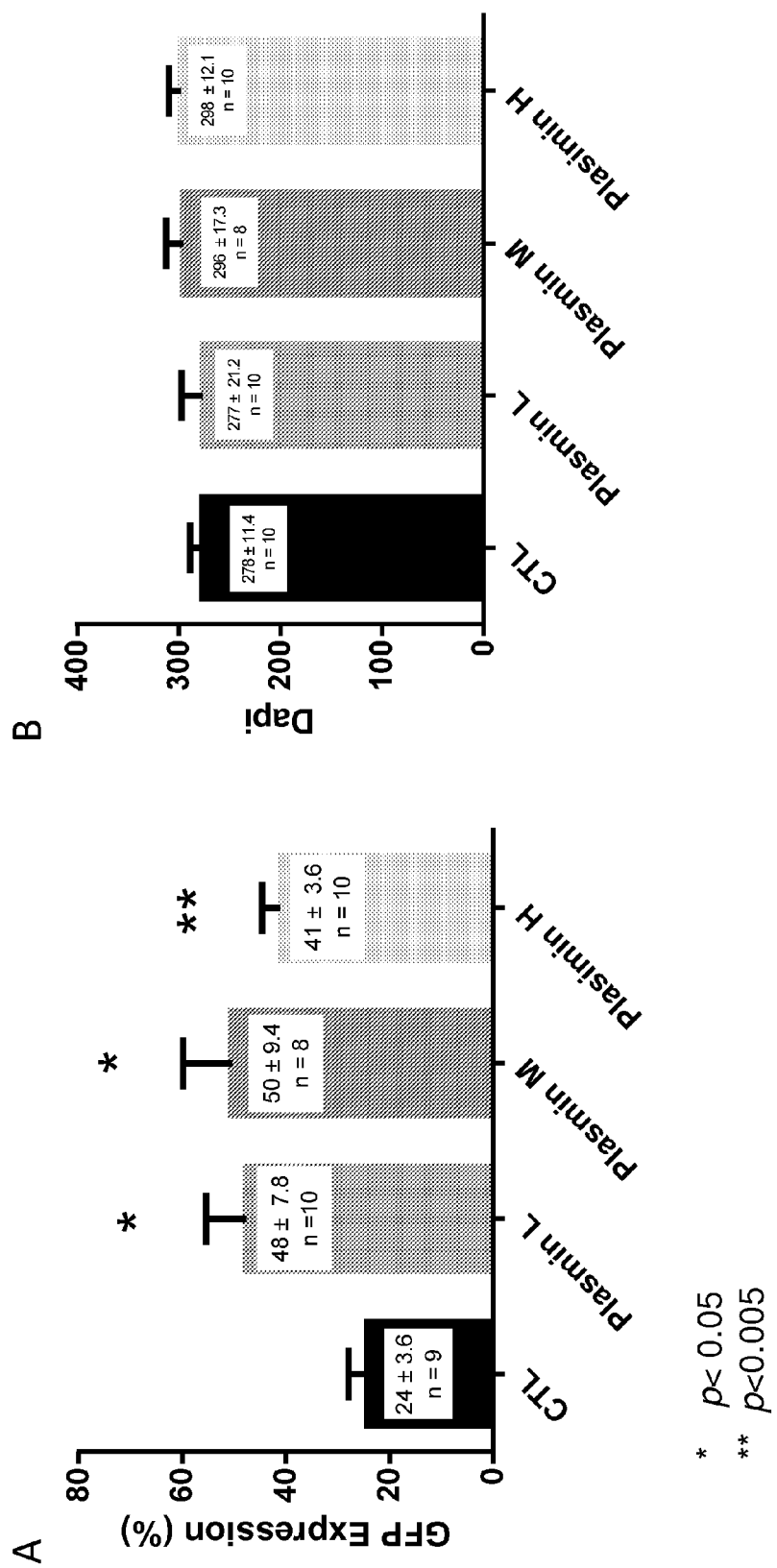
FIG. 3 is two graphs showing the quantitative assessment of the effects of plasmin on (A) AAV-mediated transduction efficiency and (B) potential neurotoxicity of plasmin in retinal ganglion cells. Co-injection of plasmin at low (L: 0.005 IU), middle (M: 0.0251U), and high (H: 0.100 IU plasmin/eye) concentrations significantly increased the AAV-mediated transduction efficiency in retinal ganglion cells (A). Co-injection of plasmin did not show any significant neurotoxicity to retinal ganglion cells. The ganglion cell counts were assessed from multiple unit areas of 223 μm×167 μm. * $p<0.05$; ** $p<0.005$.

Neurotoxicity as a result of plasmin injection was also examined. The retinal whole mounts were stained with DAPI for cell-counting. The number of cells over multiple unit areas of 223 μm×167 μm were counted and compared between control and low, middle and high doses of plasmin. As shown in FIG. 3B, the cell counts were not found to differ significantly between control and plasmin-treated retinas (p=0.74). As such, the tested concentrations of plasmin were not shown to have any neurotoxic effect to the retinal ganglion cells, thereby indicating that plasmin is safe for use in the eye, even at high doses.

Example 3

Plasmin Increases Transduction Efficiency in Retinal Bipolar Cells

Comparison of the transduction efficiency of a viral vector encoding mCherry fluorescent protein when co-injected with different concentrations of plasmin was assessed in vivo. Specifically, overall levels and the localization of mCherry expression throughout the retina were examined. An AAV2 vector with an Y444F capsid mutation carrying mCherry under control of an mGluR6 promoter were injected at a concentration of $2 \times 10^{12}$ vg/ml. The mGluR6 promoter directs expression of mCherry specifically to the retinal bipolar cells.

The AAV2 mCherry vector was co-injected with three doses of plasmin, high (H=0.100 IU/eye), middle (M=0.025 IU/eye), and low (L=0.005 IU/eye). After 1 month, the retinas were isolated and retinal whole-mounts were prepared. Transduction efficiency was evaluated by immunostaining of mCherry for immunofluorescence analysis and cell counting. Cells were counted from multiple unit areas of 223 μm×167 μm.

Figure 4:
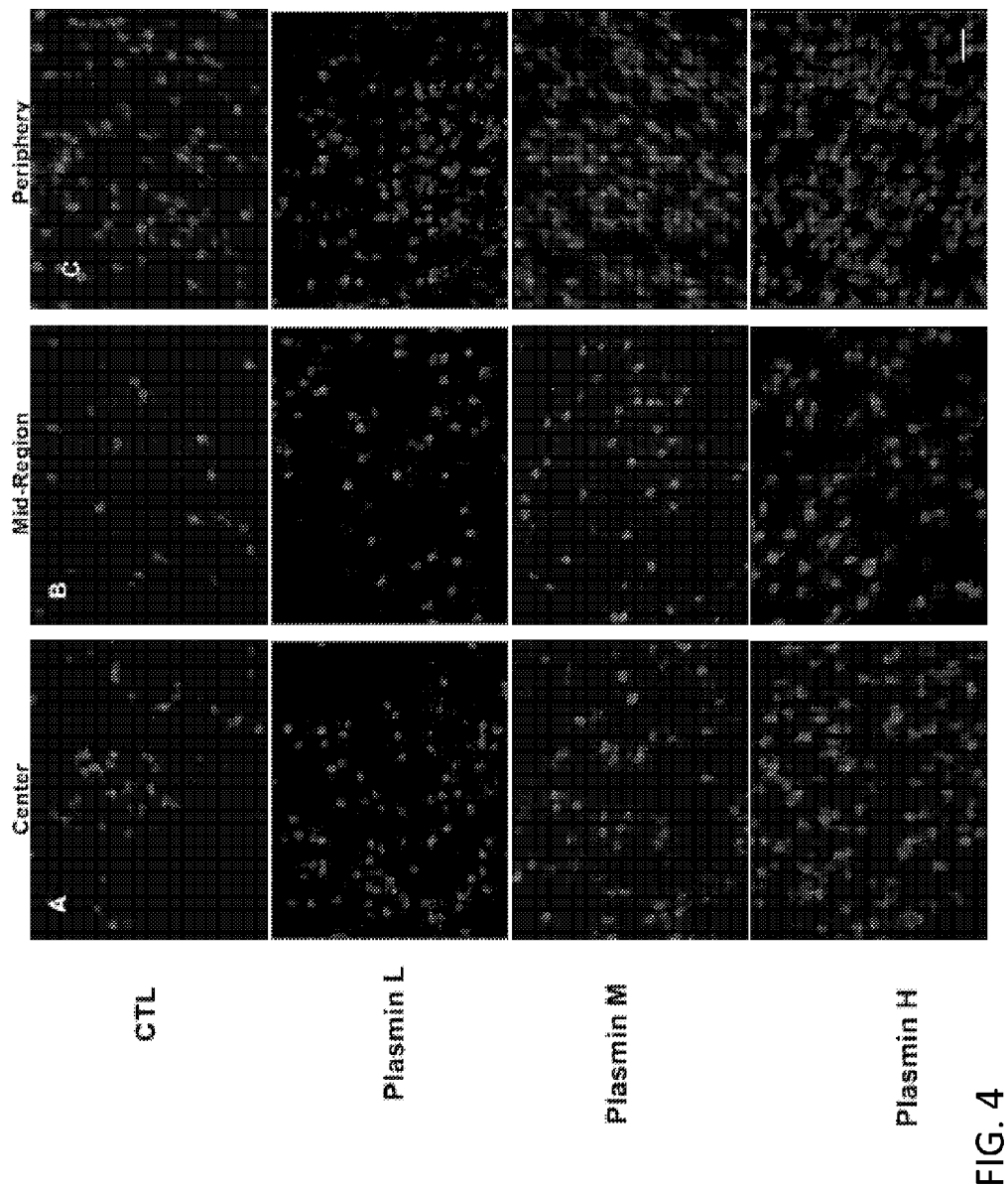
FIG. 4 is a series of representative fluorescence images of mCherry-expressing retinal bipolar cells in retinal wholemounts. AAV2 vectors ($2\times10^{12}$ vg/ml) with Y444F capsid mutation carrying mCherry under control of a mGluR6 promoter were co-injected along with plasmin of three doses (L: 0.005 IU, M: 0.025 IU, and H: 0.100 IU/eye) into the vitreous space of adult C56BL/6J mice at age of approximately one month. Transduction efficiency was evaluated one month after virus injection by immunostaining and cell counting.
Figure 5:
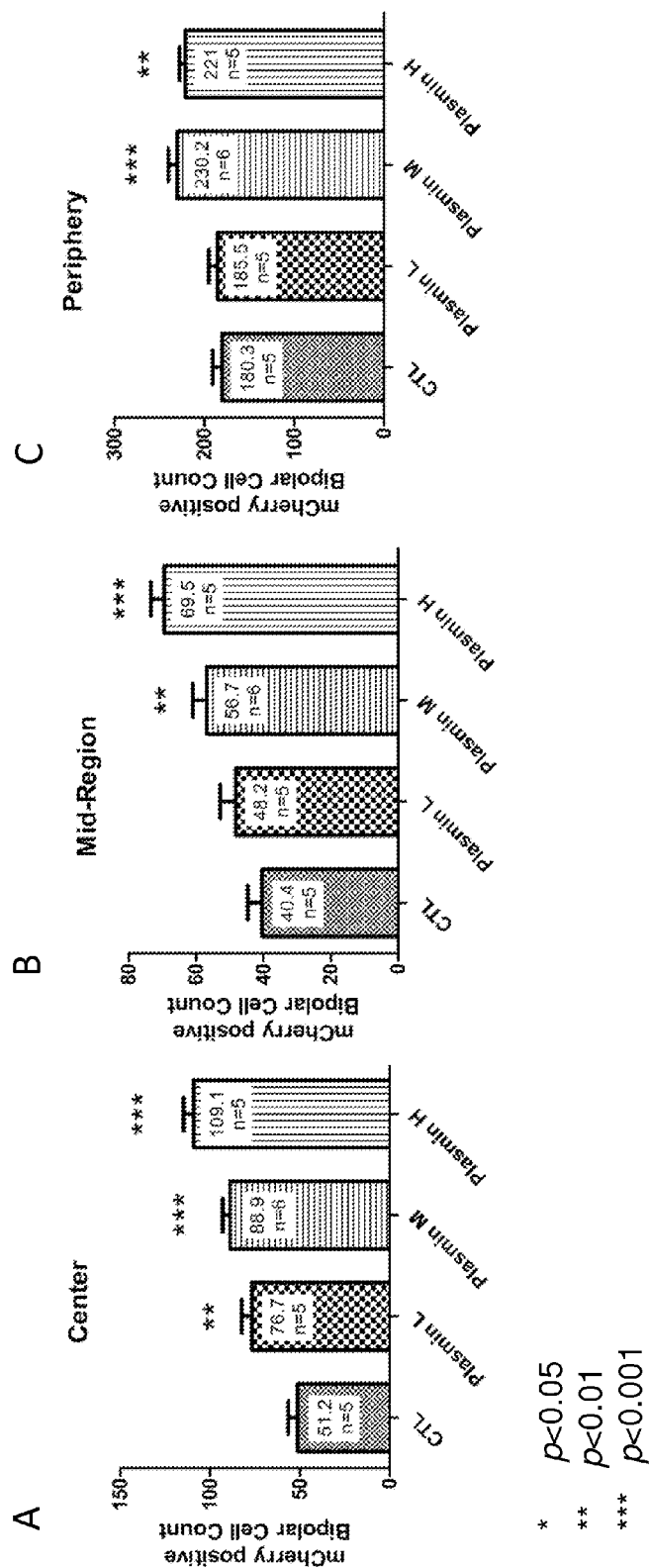
FIG. 5 is three graphs showing quantitative data for the effects of plasmin on AAV-mediated transduction efficiency in retinal bipolar cells. A) Center; B) Mid-region; and C) Periphery. The counts of mCherry expressing retinal bipolar cell were assessed from multiple unit areas of 223 μm×167 μm. *$p<0.05$; $p<0.01$; *$p<0.001$.

Injection of the vectors without plasmin did not result in uniform mCherry expression in retinal bipolar cells across the entire retina (FIG. 4, control, top panels). Transduction efficiently was low in the center (A) and middle (B) retina, but high in the periphery. Co-injection of the AAV2 mCherry vector with increasing dosages of plasmin (low, middle and high, bottom panels) resulted in increased transduction efficiency at each retinal region in a dose-dependent manner.

The qualitative results from immunofluorescence images were verified by cell counting. Quantification of mCherry-expressing cells when co-injected with or without plasmin showed that plasmin significantly increased the density of mCherry-expressing retinal cells. The increase in transduction efficiency with plasmin compared to control was statistically significant with all three doses of plasmin at the center of the retina. Middle and high doses of plasmin resulted in a statistically significant increase in mCherry expression at the mid-region and periphery of the retina. These results show that plasmin enhances transduction efficiency throughout the retina, including the peripheral, middle, and center regions of the retina.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of enhancing the delivery of a therapeutic agent to an eye of a subject comprising administering, by intravitreous injection, a plasmin or derivative thereof and the therapeutic agent to the eye, wherein the therapeutic agent comprises a nucleic acid expression vector.

2. The method of claim 1, wherein the plasmin or derivative thereof is a miniplasmin or a microplasmin (ocriplasmin).

3. The method of claim 1, wherein nucleic acid expression vector is a viral vector comprising a transgene.

4. The method of claim 3, wherein the transgene is an opsin.

5. The method of claim 4, wherein the opsin is selected from the group consisting of channelrhodopsin, halorhodopsin, melanopsin, pineal opsin, bacteriorhodopsin, and proteorhodopsin, or a functional variant thereof.

6. The method of claim 3, wherein said transgene is operably linked to a cell-specific promoter.

7. The method of any one of the preceding claims, wherein the therapeutic agent is encapsulated in a nanoparticle, a polymer, or a liposome.

8. The method of claim 1, wherein the subject is suffering from an ocular disease or disorder.

9. The method of claim 1, wherein the plasmin or derivative thereof and the therapeutic agent are delivered concurrently or sequentially.

10. The method of claim 1, wherein the therapeutic agent is delivered to a retinal cell.

11. The method of claim 10, wherein the retinal cell is a retinal ganglion cell, a retinal bipolar cell, a retinal horizontal cell, an amacrine cell, a photoreceptor cell, a Müller glial cell, or a retinal pigment epithelial cell.

12. A method of increasing light sensitivity or improving or restoring vision in a subject comprising administering a plasmin or derivative thereof and a nucleic acid expression vector that encodes an opsin to the vitreous of the eye.

13. The method of claim 12, wherein said opsin is selected from the group consisting of channelrhodopsin, halorhodopsin, melanopsin, pineal opsin, bacteriorhodopsin, and proteorhodopsin, or a functional variant thereof.

14. The method of claim 12 or 13, wherein the subject has an ocular disease or disorder.

15. The method of claim 12, wherein the plasmin or derivative thereof is a miniplasmin or a microplasmin (ocriplasmin).

16. The method of claim 12, wherein said opsin is operably linked to a cell-specific promoter.

17. The method of claim 12, wherein the plasmin or derivative thereof and the nucleic acid expression vector are delivered concurrently or sequentially.

18. The method of claim 12, wherein the nucleic acid expression vector is delivered to a retinal cell.

19. The method of claim 18, wherein the retinal cell is a retinal ganglion cell, a retinal bipolar cell, a retinal horizontal cell, an amacrine cell, a photoreceptor cell, a Müller glial cell, or a retinal pigment epithelial cell.

20. The method of claim 12, wherein the nucleic acid expression vector is a viral vector.

\* \* \* \* \*